US00PP23061P2

(12) United States Plant Patent
Hofmann

(10) Patent No.: US PP23,061 P2
(45) Date of Patent: Sep. 18, 2012

(54) ***NEMESIA* PLANT NAMED 'INTRAIREDTWO'**

(50) Latin Name: *Nemesia hybrida*
Varietal Denomination: Intrairedtwo

(75) Inventor: Silvia Hofmann, Mainz (DE)

(73) Assignee: Innovaplant GmbH + Co. KG, Gensingen (DE)

( * ) Notice: Subject to any disclaimer, the term of this patent is extended or adjusted under 35 U.S.C. 154(b) by 280 days.

(21) Appl. No.: 12/802,236

(22) Filed: Jun. 1, 2010

(51) Int. Cl.
*A01H 5/00* (2006.01)

(52) U.S. Cl. ..... Plt./458

(58) Field of Classification Search ..... Plt./458
See application file for complete search history.

(56) References Cited

U.S. PATENT DOCUMENTS

PP18,084 P2 * 9/2007 Hofman et al. ..... Plt./458
PP19,727 P2 * 2/2009 Heinrich ..... Plt./458

OTHER PUBLICATIONS

UPOV ROM GTITM Computer Database, GTI Jouve Retrieval Software 2011/04 Citation for 'Intrairedtwo'.*

* cited by examiner

*Primary Examiner* — Wendy C Haas
(74) *Attorney, Agent, or Firm* — C. A. Whealy

(57) ABSTRACT

A new and distinct cultivar of *Nemesia* plant named 'Intrairedtwo', characterized by its upright, outwardly spreading and mounding plant habit; vigorous growth habit; freely branching habit; freely flowering habit; long flowering period; and dark red-colored flowers with greyed orange-colored centers.

1 Drawing Sheet

Botanical designation: *Nemesia hybrida.*
Cultivar denomination: 'INTRAIREDTWO'.

BACKGROUND OF THE INVENTION

The present invention relates to a new and distinct cultivar of *Nemesia* plant, botanically known as *Nemesia hybrida* and hereinafter referred to by the name 'Intrairedtwo'.

The new *Nemesia* plant is a product of a planned breeding program conducted by the Inventor in Heidesheim and Gensingen, Germany. The objective of the breeding program is to create new compact *Nemesia* plants with large attractive flowers.

The new *Nemesia* plant originated from a cross-pollination made by the Inventor during the summer of 2007 in Heidesheim, Germany of a proprietary selection of *Nemesia hybrida* identified as code number N 05 82-1, not patented, as the female, or seed, parent with a proprietary selection of *Nemesia hybrida* identified as code number N 04 82-6, not patented, as the male, or pollen, parent. The new *Nemesia* plant was discovered and selected by the Inventor as a single flowering plant from within the progeny of the stated cross-pollination in a controlled environment in Heidesheim, Germany during the spring of 2008.

Asexual reproduction of the new *Nemesia* plant by terminal cuttings in a controlled environment in Gensingen, Germany since 2008, has shown that the unique features of this new *Nemesia* plant are stable and reproduced true to type in successive generations.

SUMMARY OF THE INVENTION

Plants of the new *Nemesia* have not been observed under all possible environmental conditions. The phenotype may vary somewhat with variations in environmental conditions such as temperature and light intensity without, however, any variance in genotype.

The following traits have been repeatedly observed and are determined to be the unique characteristics of 'Intrairedtwo'. These characteristics in combination distinguish 'Intrairedtwo' as a new and distinct *Nemesia* plant:

1. Upright, outwardly spreading and mounding plant habit.
2. Vigorous growth habit.
3. Freely branching habit.
4. Freely flowering habit.
5. Long flowering period.
6. Dark red-colored flowers with greyed orange-colored centers.

Plants of the new *Nemesia* differ from plants of the female parent selection primarily in the following characteristics:

1. Plants of the new *Nemesia* are more freely branching than plants of the female parent selection.
2. Plants of the new *Nemesia* and the female parent selection differ in flower color as plants of the female parent selection have white-colored flowers.

Plants of the new *Nemesia* differ from plants of the male parent selection primarily in the following characteristics:

1. Plants of the new *Nemesia* are more upright than and not as trailing as plants of the male parent selection.
2. Plants of the new *Nemesia* and the male parent selection differ in flower color as plants of the male parent selection have orange-colored flowers.
3. Plants of the new *Nemesia* flower for a longer period of time than plants of the female parent selection.

Plants of the new *Nemesia* can be compared to plants of *Nemesia hybrida* 'Intraired', disclosed in U.S. Plant Pat. No. 18,084. In side-by-side comparisons conducted in Gensin gen, Germany, plants of the new *Nemesia* differed from plants of 'Intraired' in the following characteristics:

1. Plants of the new *Nemesia* were more vigorous than plants of 'Intraired'.
2. Plants of the new *Nemesia* were more freely branching than plants of 'Intraired'.
3. Plants of the new *Nemesia* and 'Intraired' differed in flower color.
4. Plants of the new *Nemesia* were less susceptible to root pathogens than plants of 'Intraired'.

BRIEF DESCRIPTION OF THE PHOTOGRAPHS

The accompanying colored photographs illustrate the overall appearance of the new *Nemesia* plant showing the colors as true as it is reasonably possible to obtain in colored reproductions of this type. Colors in the photographs may differ slightly from the color values cited in the detailed botanical description which accurately describe the colors of the new *Nemesia* plant.

The photograph at the bottom of the sheet comprises a side perspective view of a typical flowering plant of 'Intrairedtwo' grown in a container.

The photograph at the top of the sheet is a close-up view of a typical flowering plant of 'Intrairedtwo'.

DETAILED BOTANICAL DESCRIPTION

Plants used for the aforementioned photographs and following description were grown under conditions which closely approximate commercial production conditions during the spring in 16.5-cm containers in an outdoor nursery in Bonsall, Calif. During the production of the plants, day temperatures ranged from 14° C. to 21° C., night temperatures ranged from 7° C. to 10° C. and light levels ranged from 7,000 to 10,000 foot-candles. Plants were pinched three times and were 3.5 months old when the photographs and description were taken. In the following description, color references are made to The Royal Horticultural Society Colour Chart, 2007 Edition, except where general terms of ordinary dictionary significance are used.

Botanical classification: *Nemesia hybrida* 'Intrairedtwo'.

Parentage:

*Female, or seed, parent*.—Proprietary selection of *Nemesia hybrida* identified as code number N 05 82-1, not patented.

*Male, or pollen, parent*.—Proprietary selection of *Nemesia hybrida* identified as code number N 04 82-6, not patented.

Propagation:

*Type*.—By terminal cuttings.

*Time to initiate roots, summer*.—About 10 days at 20° C.

*Time to initiate roots, winter*.—About 14 days at 20° C.

*Time to produce a rooted young plant, summer*.—About 14 days at 20° C.

*Time to produce a rooted young plant, winter*.—About 14 to 20 days at 20° C.

*Root description*.—Fine, fibrous; white in color.

*Rooting habit*.—Freely branching; dense.

Plant description:

*Plant and growth habit*.—Upright, outwardly spreading and mounding plant habit; vigorous growth habit; freely branching habit; about six to seven primary branches develop per plant with numerous secondary laterals.

*Plant height*.—About 28 cm.

*Plant diameter*.—About 42 cm.

Lateral branch description:

*Length*.—About 27 cm.

*Diameter*.—About 4 mm.

*Internode length*.—About 3 cm to 3.5 cm.

*Strength*.—Strong.

*Aspect*.—Mostly upright to outwardly spreading.

*Texture*.—Smooth, glabrous.

*Color*.—Close to 146B.

Foliage description:

*Arrangement*.—Opposite, simple.

*Length*.—About 4.8 cm.

*Width*.—About 1.7 cm.

*Shape*.—Lanceolate.

*Apex*.—Acute.

*Base*.—Attenuate.

*Margin*.—Serrate.

*Texture, upper and lower surfaces*.—Smooth, glabrous.

*Venation pattern*.—Pinnate; arcuate.

*Color*.—Developing leaves, upper surface: Close to 137B. Developing leaves, lower surface: Close to 146B. Fully expanded leaves, upper surface: Close to 137A; venation, close to 137C. Fully expanded leaves, lower surface: Close to 146B; venation, close to 146B.

*Petioles*.—Length: About 4 mm. Diameter: About 5 mm. Texture, upper and lower surfaces: Smooth, glabrous. Color, upper surface: Close to N144A. Color, lower surface: Close to 146B.

Flower description:

*Flower arrangement and habit*.—Bilabiate single flowers arranged in loose terminal racemes; flowers develop acropetally towards the apex; flowers face upright to outwardly; freely flowering habit with about 24 flowers per inflorescence.

*Fragrance*.—None detected.

*Natural flowering season*.—Long flowering period, in California, plants flower from May through September; flowering continuous during this period.

*Flower longevity*.—Flowers last about four to five days on the plant; flowers not persistent.

*Inflorescence height*.—About 5.5 cm to 9 cm.

*Inflorescence diameter*.—About 4.5 cm to 5 cm.

*Flower width*.—About 2.4 cm.

*Flower length*.—About 2.6 cm.

*Flower depth*.—About 1.4 cm.

*Flower buds*.—Length: About 8 mm. Diameter: About 5 mm. Shape: Oval with a short spur. Color: Close to 183D.

*Petals*.—Arrangement: Five petals; two upper and two lateral petals fused at base to form an upright lobed and arched upper or banner lip; lower petal modified into a large lower lip with convex oval protuberance and short nectar spur. Shape: Oval to rounded. Apex: Rounded. Margin: Entire. Length: Upper petals: About 1 cm. Lateral petals: About 1 cm. Lower petal: About 1.5 cm. Width: Upper petals: About 6 mm. Lateral petals: About 7 mm. Lower petal: About 1.9 cm. Texture, upper and lower surfaces: Smooth, glabrous; protuberance on lower lip is pubescent. Color: When opening, upper surface: Close to N34A. When opening, lower surface: Close to 183B to 183C. Fully opened, upper surface: Close to 53A; protuberance, close to 175A to 175B; thin streaks at base of upper petals, close to N186C. Fully opened, lower surface: Close to 183B to 183C; nectar spur, close to 195B. Throat: Close to NN155C.

*Sepals*.—Arrangement: Calyx star-shaped with five sepals fused at the base. Length: About 3 mm. Width: About 1.5 mm. Shape: Elliptical. Apex: Acute; recurved. Margin: Entire. Texture, upper and lower surfaces: Pubescent. Color, upper and lower surfaces: Close to 146A.

*Peduncles*.—Length: About 5 cm. Diameter: About 2 mm. Angle: Erect to about 45° from vertical depending on position. Strength: Strong. Texture: Sparsely pubescent. Color: Close to 146A.

*Pedicels*.—Length: About 1.5 cm. Diameter: About 1 mm. Angle: About 30° to 45° from peduncle axis. Strength: Strong. Texture: Sparsely pubescent. Color: Close to 146A.

*Reproductive organs*.—Stamens: Quantity/arrangement: Four per flower. Filament length: About 3 mm. Filament color: Close to 157D. Anther shape: Oval. Anther length: Less than 1 mm. Anther color: Close to 160D. Pollen amount: Scarce. Pollen color: Close to 13B. Pistils: Quantity: One per flower. Pistil length: About 2.5 mm. Style length: About 1 mm. Style color: Close to 145C. Stigma shape: Rounded. Stigma color: Close to 145B. Ovary color: Close to 144A.

*Seed/fruit*.—Seed and fruit development have not been observed on plants of the new *Nemesia*.

Pathogen/pest resistance: Plants of the new *Nemesia* have not been observed to be resistant to pests and pathogens common to *Nemesia* plants.

Garden performance: Plants of the new *Nemesia* have been observed to have good garden performance and to tolerate wind and rain and temperatures ranging from about 1° C. to about 30° C.

It is claimed:

1. A new and distinct *Nemesia* plant named 'Intrairedtwo' as illustrated and described.

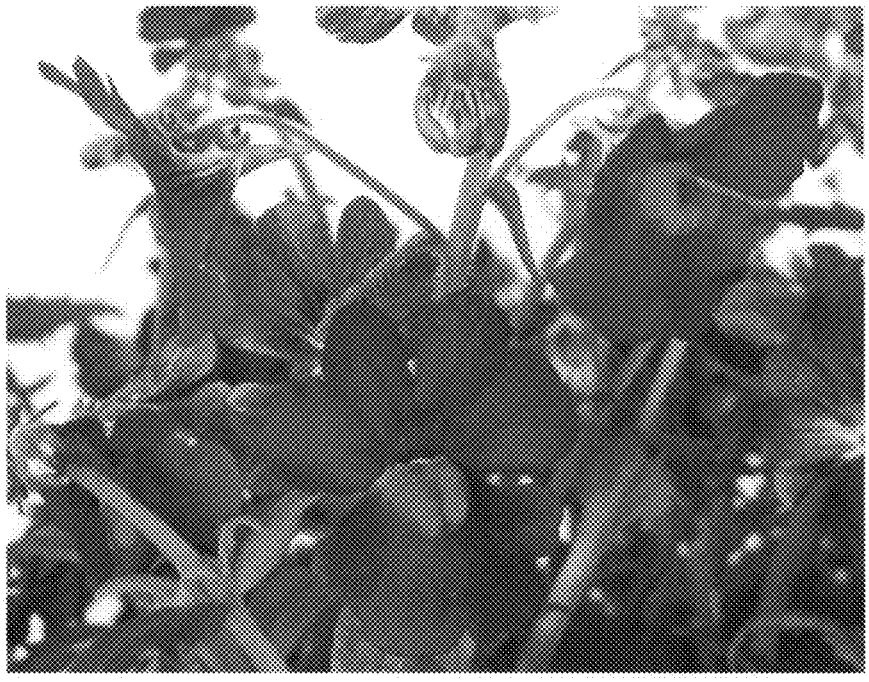
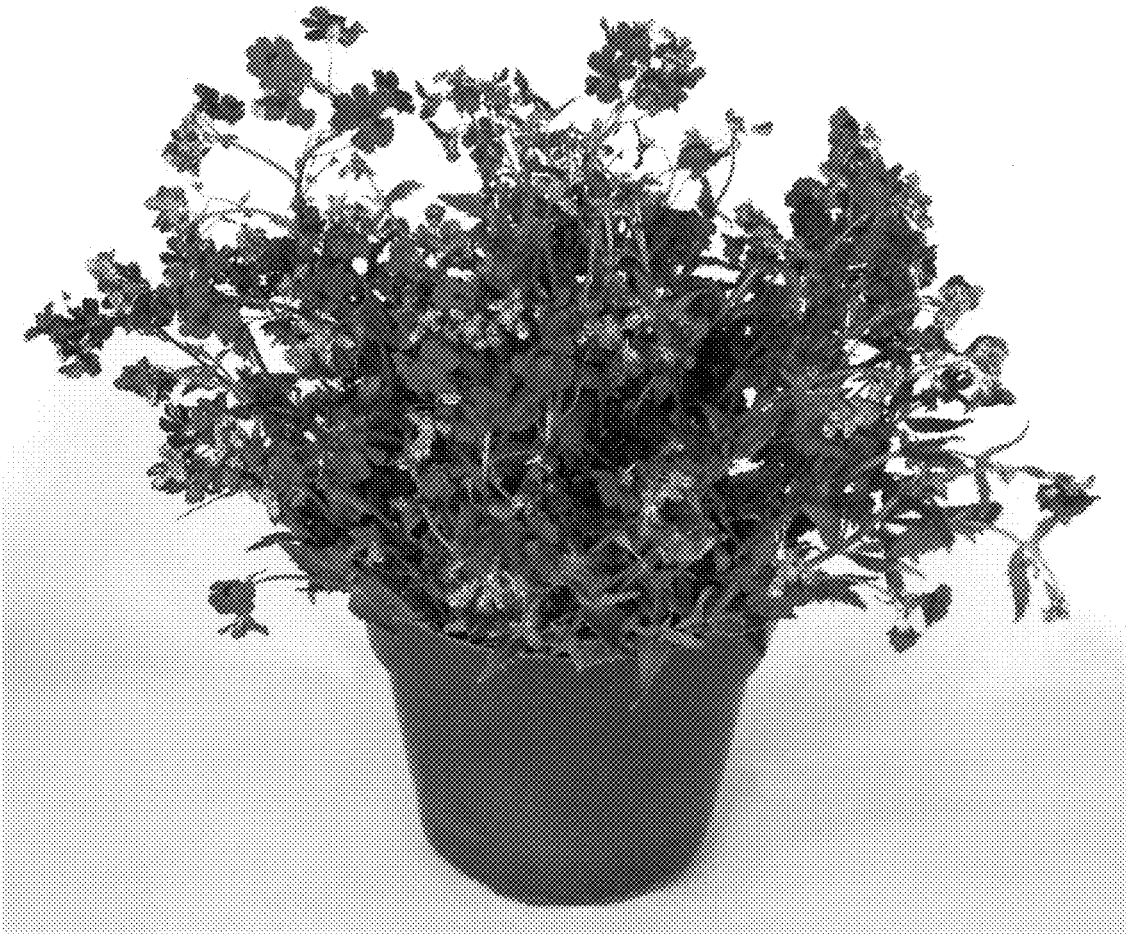

* * * * *